United States Patent [19]

Junino et al.

[11] Patent Number: 5,571,700
[45] Date of Patent: Nov. 5, 1996

[54] PROCESS FOR PREPARING MELANIN PIGMENTS BY BIOCONVERSION AND USE OF THE PIGMENTS OBTAINED IN COSMETICS

[75] Inventors: Alex Junino, Livry-Gargan; Pascal Hilaire, Tours; Richard Martin, Rochecorbon, all of France

[73] Assignee: L'Oreal, Paris, France

[21] Appl. No.: 256,576

[22] PCT Filed: Nov. 19, 1993

[86] PCT No.: PCT/FR93/01138

§ 371 Date: Jul. 18, 1994

§ 102(e) Date: Jul. 18, 1994

[87] PCT Pub. No.: WO94/12653

PCT Pub. Date: Jun. 9, 1994

[30] Foreign Application Priority Data

Nov. 20, 1992 [FR] France .................... 92 14000

[51] Int. Cl.⁶ .................. C12P 21/00; C12P 17/00; A61K 7/00
[52] U.S. Cl. .................. 435/70.1; 424/59; 424/69; 424/70.6; 424/74; 424/115; 435/41; 514/415
[58] Field of Search .............. 435/41, 70.1; 424/69, 424/74, 115, 59, 70.6; 514/415

[56] References Cited

U.S. PATENT DOCUMENTS

| | | | |
|---|---|---|---|
| Re. 33,993 | 7/1992 | Grollier et al. | 424/74 |
| 4,459,285 | 10/1984 | Grollier et al. | 424/74 |
| 4,569,839 | 2/1986 | Grollier et al. | 424/74 |
| 4,581,230 | 4/1986 | Grollier et al. | 424/74 |
| 4,746,510 | 5/1988 | Grollier et al. | 424/74 |
| 4,767,618 | 8/1988 | Grollier et al. | 424/74 |
| 4,880,621 | 11/1989 | Grollier et al. | 424/74 |
| 4,933,177 | 6/1990 | Grollier et al. | 424/74 |
| 4,961,754 | 10/1990 | Grollier | 8/423 |
| 5,205,837 | 4/1993 | Andrean et al. | 8/405 |

FOREIGN PATENT DOCUMENTS

| | | |
|---|---|---|
| 467767 | 1/1992 | European Pat. Off. . |
| 83173 | 6/1981 | Luxembourg . |

OTHER PUBLICATIONS

Chemical Abstracts, No. 43036h, vol. 102, No. 5, 4 Feb. 1985.

Primary Examiner—Herbert J. Lilling
Attorney, Agent, or Firm—Jacobson, Price, Holman & Stern, PLLC

[57] ABSTRACT

The present invention relates to a method for the preparation of a melanic pigment by enzymatic bioconversion, implementing a melanin precursor substrate and plant cells, characterized in that: (a) poppy (*Papaver somniferum*) plant cells previously cultivated are separated from their culture medium and subcultured in a culture medium with a concentration from 10 to 100 g/l; (b) the cells are ground at least partially, before or at the end of the latency time, (c) the at least partially ground cells are placed in a bioconversion medium in the presence with a melanin precursor substrate selected amoung indol, indolin, dihydroxyphenylalanin, tyramin and tyrosin; (d) the precipitated melanic pigment is collected. The invention also relates to the utilization of such resulting pigments for the preparation of cosmetic compositions.

9 Claims, No Drawings

PROCESS FOR PREPARING MELANIN PIGMENTS BY BIOCONVERSION AND USE OF THE PIGMENTS OBTAINED IN COSMETICS

The present invention relates to a process for preparing melanin pigments by bioconversion, to the pigments obtained and also to their use in the field of cosmetics.

It is known to use colored pigments in the cosmetics field, and these are essentially inorganic pigments or alternatively pigments derived from synthetic direct dyes and, in the case of black pigments, pure carbon.

It is, in particular, known to produce yellow-brown dyes by oxidation of 5-hydroxyindole. It is known, moreover, to prepare melanin pigments enzymatically, by oxidative polymerization of 5,6-dihydroxyindole derivatives such as 5,6-dimethoxyindole or 5,6-methylenedioxyindole.

The Applicant has now discovered that melanin pigments could be obtained rapidly by bioconversion of simple substrates, in particular using plant cells cultured in vitro in a standard manner.

In effect, the processes proposed to date employ conventional precursors of melanin biosynthesis, which prove expensive.

In contrast, according to the invention, the materials employed are common precursors and biological compounds which are modestly priced and easy to use. The mechanism of enzymatic bioconversion according to the invention does not employ polyphenol oxidases.

Thus, the present invention leads to a process for preparing melanin pigments by enzymatic bioconversion, employing a melanin precursor substrate and plant cells. According to the invention:

a) poppy (*Papaver somniferum*) plant cells previously cultured, are separated from their culture medium and subcultured in a culture medium at a concentration ranging from 10 to 100 g/l, b) the cells are at least partially ground before or at the end of the latency time, c) the at least partially ground cells are brought into contact, in a bioconversion medium, with a melanin precursor substrate chosen from indole, indoline, dihydroxyphenylalanine, tyramine and tyrosine, d) the precipitated melanin pigment is recovered.

In a first step, undifferentiated poppy cells are cultured in vitro in a standard culture medium. After a sufficient growth time, the cells are separated from their medium, for example by filtration. The duration of the growth time of the cells is of no importance to the process, and depends in particular on the quantity of cells which it is desired to obtain.

As a standard culture medium, Heller's medium may be used. This medium can optionally contain vitamins and/or hormones in addition.

Undifferentiated poppy cells are understood to mean cell cultures derived from fragments of whole plants, decontaminated and placed on solid culture media chosen in such a way that the cells multiply thereon without giving rise to organized tissue forms. These cells are then transferred to liquid media, where their growth takes place by simple cell multiplication. These cultures are comparable to those of bacteria.

In a second step, the cells obtained are subcultured in a standard culture medium, at a concentration of fresh cellular matter of 10 to 100 g/l. As culture medium for the subculturing, a new culture medium is used. For the subculturing, a Heller's medium optionally containing vitamins and/or hormones may also be used. The cells are maintained in this medium for a period not exceeding the latency time.

The latency time is the time needed for a freshly subcultured cell to adapt to the medium, and during which the cell concentration remains constant before growing therein. By taking periodic samples, it is thus possible to establish that the cell concentration remains substantially identical to the initial concentration—the cells are in the latency period—then the concentration grows significantly when the latency time has ended; the cells have then passed into the growth step. Depending on the strain used, the latency time can vary between 6 hours and 7 days.

It is preferable to subculture the cells at a concentration of fresh cellular matter of 20 to 50 g/l.

In a third step, before or at the end of the latency time, the cells are preferably ground to obtain a ground cell preparation.

Cell grinding may be performed in the culture medium itself, but it is preferable to isolate the cells beforehand, by filtration for example. To obtain the ground cell preparation, standard means such as a Potter or Ultra Turrax mill may be used. Preferably, grinding takes place at low temperature, and especially between 0° and 15° C.

In a fourth step, to carry out the bioconversion, the ground cell preparation is brought into contact with the melanin precursor substrate chosen from indole, indoline, dihydroxyphenylalanine (DOPA), tyramine and tyrosine. Preferably, the contacting takes place at a temperature of between 10° and 70° C.

The bioconversion medium can consist of the ground cell preparation. It is also possible to take up the ground cell preparation in demineralized water or in a buffered solution. In this case, the pH is preferably chosen to be between 3 and 9.

The reaction is performed by bringing the substrate and the ground cell preparation into contact, preferably in a buffered medium, it being possible for the substrate concentration to vary within wide limits, this concentration being dependent on the solubility of the substrate in the aqueous medium.

The reaction is preferably carried out with stirring.

The substrate concentration is generally between 10 mg and 2 g per liter of buffered solution containing from 20 to 200 g of fresh cellular matter. The substrate concentration may be increased by dissolving the substrate in a water-miscible organic solvent such as ethanol.

In this bioconversion step, the reaction time is variable and depends, in particular on the substrate, reaction temperature and the pH of the medium.

Generally speaking, a black precipitate appears after 30 minutes to 24 hours. The precipitated pigment may be recovered by decantation, filtration or centrifugation, or any other suitable means of separation. The filtrate may be recovered and the operation begun again by adding substrate thereto, under the conditions described above. Preferably, the medium is filtered through a screen of mesh size less than 5 μm in order, in particular, to free the pigments from proteinaceous residues.

Analysis of this pigment by EPR (electron paramagnetic resonance), performed using a BRUCKER ER 200 D spectrometer at 9.52 GHz with a field modulation frequency of 100 KHz [sic] and a microwave power of 1.9 mw [sic], reveals a maximum absorption at about 3470 gauss, characteristic of melanins.

The melanin pigment obtained can then be washed with ethanol and thereafter with water in order to remove the melanin precursor.

The pigments obtained, where appropriate washed and dried, are especially useful in the cosmetics field, for the preparation of makeup products, sun composition products or alternatively hair dyeing composition products.

They may be introduced for the purpose of these applications into a cosmetically acceptable medium based on water and/or on a water/organic solvent mixture or on one or more solvent(s), and optionally also containing other additives which are common in cosmetics, for example surfactants, thickeners, preservatives.

According to a variant of the invention, the melanin pigment may be deposited on an inorganic filler consisting of inert particles having a particle size which is standard for these carriers, for example a particle size of less than 20 μm, and preferably 10 μm.

In a known manner, the pigment may be deposited and/or absorbed on inorganic particles in lamellar or non-lamellar form, lamellar or non-lamellar organic particles, colored or otherwise. These particles have an average particle size of between 0.01 and 200 μm.

Colored powders which may be used in cosmetics are thereby obtained.

This colored powder may be prepared by dispersing the inorganic or organic particles in the solution of melanin precursor and of ground cell preparation in which the above bioconversion takes place. The powder containing the pigment is separated, for example by filtration, after the reaction time needed for the formation of the melanin pigments, washed with water and dried.

These powders may also be prepared by absorption of the melanin pigment prepared according to the invention on and/or in the inorganic or organic particles defined above.

In this variant, it is possible to carry out the process by dispersing the melanin pigment previously formed in a medium in which the particles are insoluble and containing said particles, and, after absorption of the pigment, the pigmented particles are dried.

Calcium carbonate, silica or titanium oxide particles having the particle size defined above may be used as inorganic fillers.

As organic fillers, it is preferable to use particles of polymers derived from keratin, optionally modified, of polymers derived from chitin, optionally deacetylated, of silk fibroin, of synthetic polymers chosen from crosslinked poly-(methyl methacrylate) and crosslinked poly-β-alanine, hollow microspheres of copolymers of vinylidine chloride and acrylonitrile or alternatively porous microspheres of polyamide-12, polyamide-6 or of copolyamide-6/12, as well as silicone powders consisting of gums, resins, organopolysiloxane elastomers.

These particles have a particle size which is preferably greater than 0.1 μm.

The lamellar particles are inorganic or organic particles which take the form of lamellae, optionally stratified. These lamellae are characterized by a thickness which is smaller than the largest dimension. Preferably, the ratio of the largest dimension to the thickness is between 2 and 100. The largest dimension is generally less than 100 μm.

The examples which follow are designed to illustrate the invention, no limitation, however, being implied.

Examples of preparation of a melanin pigment from indole

Different strains derived from undifferentiated poppy cultures are used, these strains having been taken up in a liquid medium from calluses on agar, and the following steps are carried out.

1st step

Undifferentiated poppy cells are cultured in vitro at 26° C. in the following media defined below:

| MEDIUM 1 | | |
|---|---|---|
| KCl | 0.750 g/l | Heller's macronutrients |
| NaNO$_3$ | 0.600 g/l | Heller's macronutrients |
| MgSO$_4$.7H$_2$O | 0.250 g/l | Heller's macronutrients |
| NaH$_2$PO$_4$.2H$_2$O | 0.141 g/l | Heller's macronutrients |
| CaCl$_2$.2H$_2$O | 0.075 g/l | Heller's macronutrients |
| ZnSO$_4$.7H$_2$O | 1 mg/l | Heller's macronutrients |
| H$_3$BO$_3$ | 1 mg/l | Heller's macronutrients |
| MnSO$_4$.1H$_2$O | 0.075 mg/l | Heller's macronutrients |
| CuSO$_4$.5H$_2$O | 0.03 mg/l | Heller's macronutrients |
| AlCl$_3$.6H$_2$O | 0.05 mg/l | Heller's macronutrients |
| Kl [sic] | 0.01 mg/l | Heller's macronutrients |
| NiCl$_2$.6H$_2$O | 0.03 mg/l | Heller's macronutrients |
| FeCl$_3$.6H$_2$O | 1.00 mg/l | |
| Morel's vitamins | 2 ml | |
| 2,4-Dichlorophenoxy-acetic acid $10^{-4}$ M | 1 ml | |
| Kinetin $10^{-3}$ M | 1 ml | |
| Glucose | 30 g/l | |

| MEDIUM 2 | | |
|---|---|---|
| KCl | 0.750 g/l | Heller's macronutrients |
| NaNO$_3$ | 0.600 g/l | Heller's macronutrients |
| MgSO$_4$.7H$_2$O | 0.250 g/l | Heller's macronutrients |
| NaH$_2$PO$_4$.2H$_2$O | 0.141 g/l | Heller's macronutrients |
| CaCl$_2$.2H$_2$O | 0.075 g/l | Heller's macronutrients |
| ZnSO$_4$.7H$_2$O | 1 mg/l | Heller's macronutrients |
| H$_3$BO$_3$ | 1 mg/l | Heller's macronutrients |
| MnSO$_4$.1H$_2$O | 0.076 mg/l | Heller's macronutrients |
| CuSO$_4$.5H$_2$O | 0.03 mg/l | Heller's macronutrients |
| AlCl$_3$.6H$_2$O | 0.05 mg/l | Heller's macronutrients |
| Kl [sic] | 0.01 mg/l | Heller's macronutrients |
| NiCl$_2$.6H$_2$O | 0.03 mg/l | Heller's macronutrients |
| FeCl$_3$.6H$_2$O | 1.00 mg/l | |
| Glucose | 30 g/l | |

| MEDIUM 3 | | |
|---|---|---|
| KCl | 1.500 g/l | |
| KNO$_3$ | 1.450 g/l | |
| (NH$_4$)$_2$SO$_4$ | 0.134 g/l | |
| KH$_2$PO$_4$ | 0.150 g/l | |
| MgSO$_4$.7H$_2$O | 0.500 g/l | |
| CaCl$_2$.2H$_2$O | 0.150 g/l | |
| ZnSO$_4$.7H$_2$O | 1 mg/l | Heller's micronutrients |
| H$_3$BO$_3$ | 1 mg/l | Heller's micronutrients |
| MnSO$_4$.1H$_2$O | 0.076 mg/l | Heller's micronutrients |
| CuSO$_4$.5H$_2$O | 0.03 mg/l | Heller's micronutrients |
| AlCl$_3$.6H$_2$O | 0.05 mg/l | Heller's micronutrients |
| Kl [sic] | 0.01 mg/l | Heller's micronutrients |
| NiCl$_2$.6H$_2$O | 0.03 mg/l | Heller's micronutrients |
| FeCl$_3$.6H$_2$O | 1.00 mg/l | |
| Morel's vitamins | 2 ml | |
| 2,4-Dichlorophenoxy-acetic acid $10^{-4}$ M | 1 ml | |
| Kinetin $10^{-3}$ M | 1 ml | |
| Glucose | 30 g/l | |

Morel's vitamins are understood to mean a mixture containing, per 100 ml:

| | |
|---|---|
| Ca panthotenate [sic] | 0.050 g |
| Nicotinic acid | 0.050 g |

|  |  |
| --- | --- |
| Meso-Inositol | 5.000 g |
| Pyridoxine (B6) | 0.050 g |
| Thiamine (B1) | 0.050 g |
| Biotin | 0.5 mg |

Of eight strains tested, four were cultured in medium 1, three in medium 2 and one in medium 3.

After a growth time enabling the cell concentration to reach 400 g/l of medium, the cells are recovered by filtration on 50 μm.

2nd step

The cells obtained in the first step are subcultured in an identical culture medium at 4° C. on the basis of 50 g/l. After a latency time varying between 1 and 2 days, the cells are filtered off.

3rd step

The cells are ground at 4° C. in a Potter. The ground preparation is taken up in a buffered medium having a pH of between 6.5 and 7, on the basis of approximately 1 g of cell per 10 ml of buffer solution.

4th step 50 mg of indole per liter of solution obtained in the third step are added with stirring and at room temperature. Once the first fifteen minutes have elapsed, a pink coloration appears; this coloration becomes mauve, and ultimately black at the end of two hours. This suspension is then filtered through a screen of mesh size less than 5 microns. The precipitate is then washed with water and thereafter dried.

From the eight strains tested after culture in each of the three media described, pigments were obtained, whereas these three culture media do not give any reaction with the same precursor either before or after culturing of the cells.

EPR analysis of the pigments obtained:

The EPR spectrum displays an absorption maximum at 3470 gauss.

APPLICATION EXAMPLES

EXAMPLE A: CREAM MASCARA

|  |  |
| --- | --- |
| Black pigment obtained according to Example 1 | 15 g |
| Triethanolamine stearate | 15 g |
| Candellila [sic] wax | 8 g |
| Carnauba wax | 10 g |
| Hydroxyethylcellulose | 0.9 g |
| Keratin hydrolysate (expressed as dry substance) | 0.75 g |
| Preservatives qs | |
| Water qs | 100 g |

EXAMPLE B: HAIR GEL

|  |  |
| --- | --- |
| Black pigment obtained according to Example 1 | 0.5 g |
| Vinylpyrrolidone/vinyl acetate copolymer sold under the name "PVP/VA S 630" by the company GAF | 1.5 g |
| Ethyl alcohol | 15 g |
| "Carbopol 940" (GOODRICH CHEMICAL) | 0.7 g |
| Triethanolamine qs | pH = 7.5 |
| Preservatives qs | |
| Water qs | 100 g |

We claim:

1. Process for preparing a melanin pigment by enzymatic bioconversion, employing a melanin precursor substrate and plant cells, comprising:

a) separating poppy (*Papaver somniferum*) plant cells previously cultured from their culture medium and subculturing the separated poppy plant cells in a culture medium at a concentration ranging from 10 to 100 g/l, b) at least partially grinding the cells before or at the end of the latency time, c) bringing the at least partially ground cells into contact, in a bioconversion medium, with a melanin precursor substrate selected from the group consisting of indole, indoline, dihydroxyphenylalanine, tyramine and tyrosine, and d) recovering precipitated melanin pigment.

2. Process according to claim 1, wherein the culture medium in which the previously cultured cells are subcultured has a concentration of between 20 and 50 g/l.

3. Process according to claim 1, wherein the substrate is brought into contact with a ground cell preparation.

4. Process according to claim 3, wherein the ground cell preparation is obtained by grinding the cells, previously separated from their culture medium, at a temperature of between 0° and 15° C.

5. Process according to one of claim 1, wherein the contacting of the at least partially ground cells with the substrate is carried out with stirring.

6. Process according to claim 1, wherein the contacting of the at least partially ground cells with the substrate takes place at a temperature of between 10° and 70° C.

7. Process according to claim 1, wherein the contacting of said cells with said substrate is carried out in a buffered solution having a pH between 3 and 9.

8. Process according to claim 1, wherein the precipitated pigment is recovered by filtration, decantation or centrifugation.

9. Process according to claim 8, wherein the precipitated pigment is recovered by filtration of the bioconversion medium through a screen of mesh size less than 5 μm.

* * * * *